United States Patent [19]
Conte

[11] Patent Number: 5,772,623
[45] Date of Patent: Jun. 30, 1998

[54] BANDAGE HAVING A TAB PORTION FOR FACILITATING EASY REMOVAL FROM THE SKIN

[76] Inventor: Stephen Conte, R.D. 2 Box 92-2, Oxford, N.Y. 13830

[21] Appl. No.: 513,455

[22] Filed: Aug. 10, 1995

[51] Int. Cl.$^6$ ....................................................... A61F 5/00
[52] U.S. Cl. ............................................................. 602/57
[58] Field of Search .................................... 206/440, 441; 220/270, 354, 793, 805; 215/232, 341, 349, 308; 602/41–59

[56] References Cited

U.S. PATENT DOCUMENTS 4,641,643   2/1987   Greer ...................................... 602/42 X
5,086,763   2/1992   Hathman ................................... 602/42

FOREIGN PATENT DOCUMENTS 9424972   11/1994   WIPO ....................................... 602/52

Primary Examiner—Richard J. Apley
Assistant Examiner—Kim M. Lee
Attorney, Agent, or Firm—George R. McGuire

[57] ABSTRACT

A flat, adhesive bandage having a lower, skin contacting surface coated with a first adhesive, and an upper surface partially coated with a second adhesive. At least one tab integrally extends from one edge of the bandage and is releasably adhered to the upper surface in complete covering relation to the second adhesive and in covering relation to an uncoated portion of the upper surface. When it is desired to remove the bandage from the skin, the tab may be grasped and lifted away from the upper surface. The tab may then be pulled in a direction to effectively remove the bandage. Therefore, it is not necessary to pry between the skin and the bandage's lower surface to effect removal of the bandage.

19 Claims, 4 Drawing Sheets

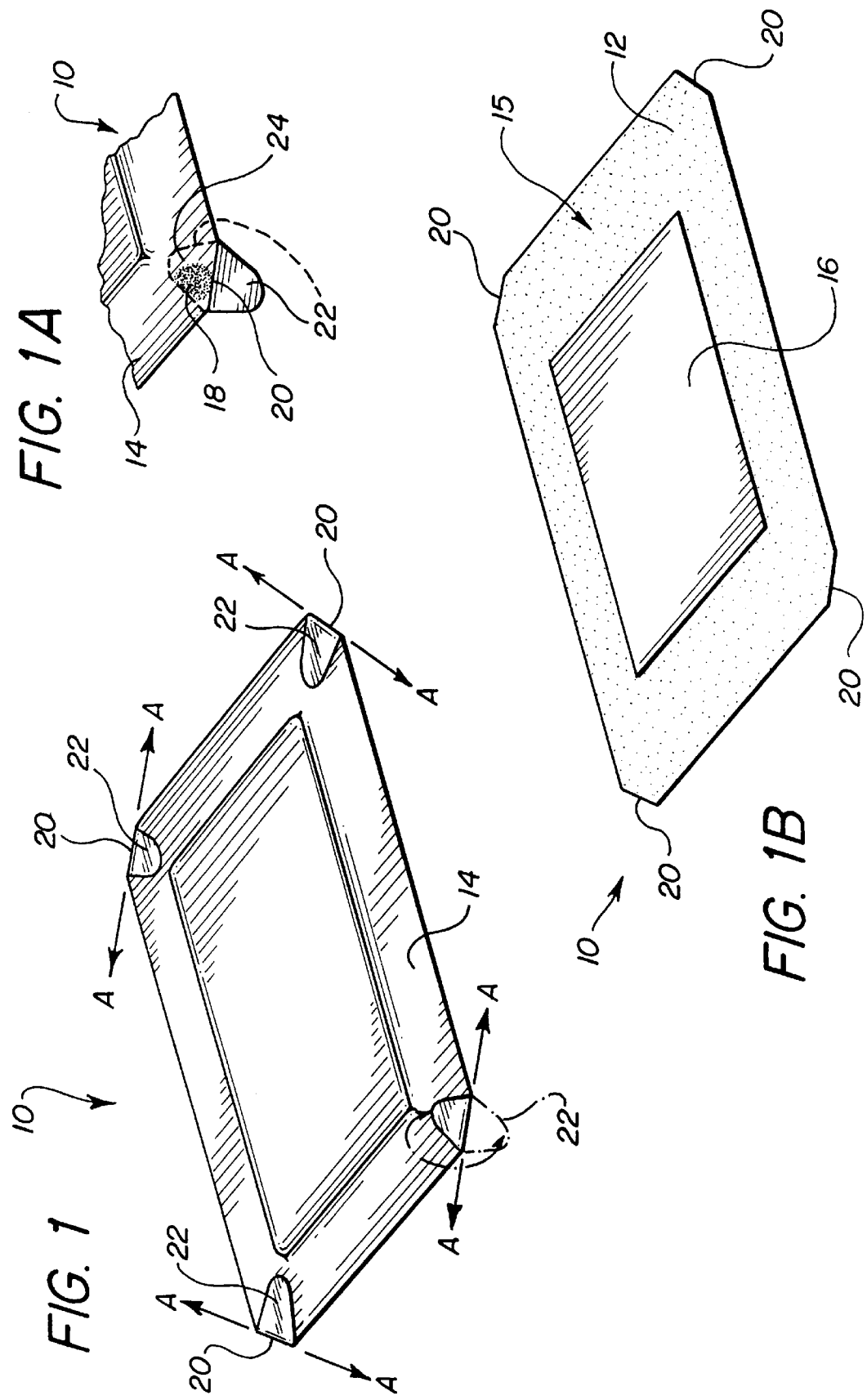

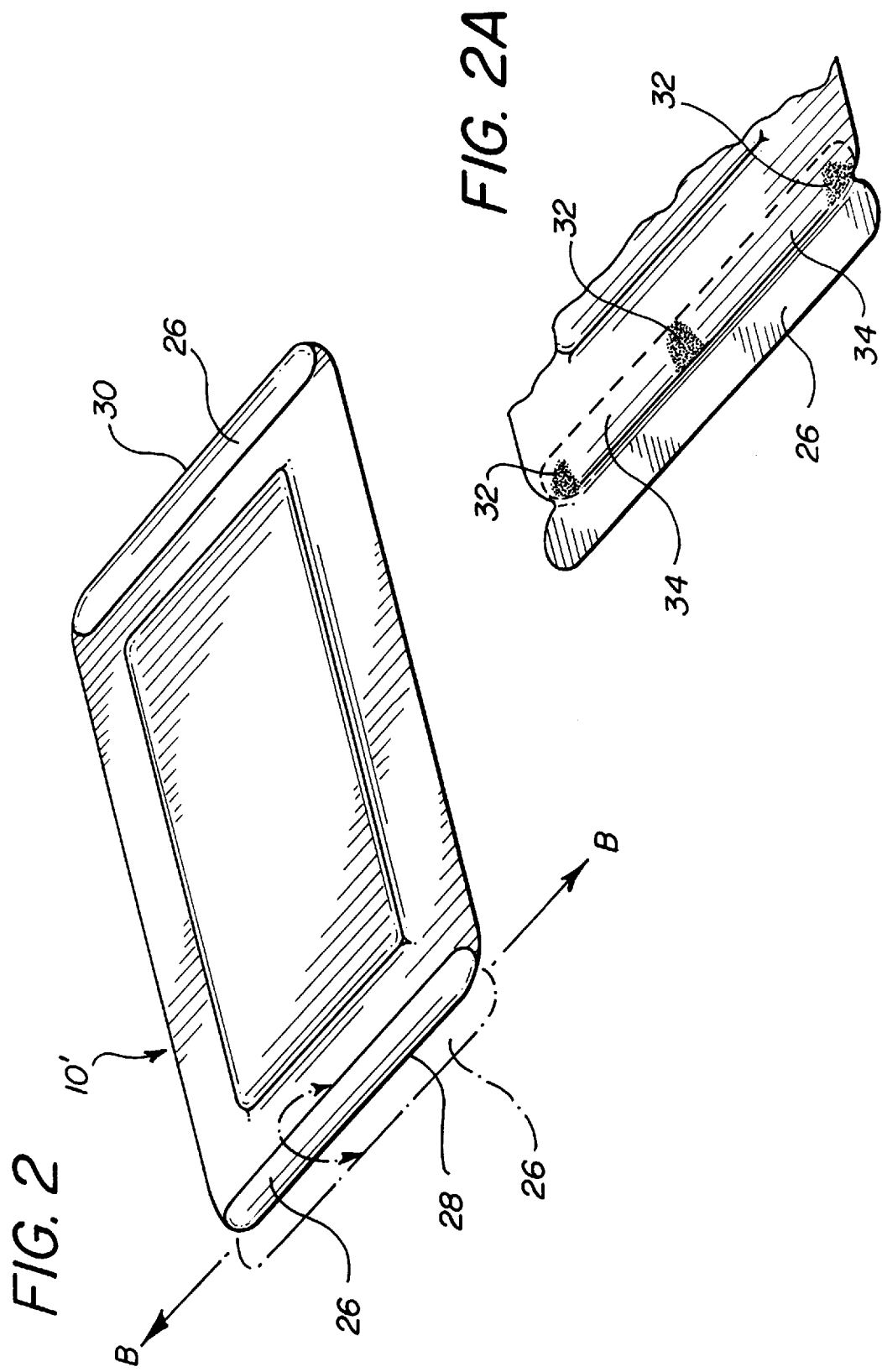

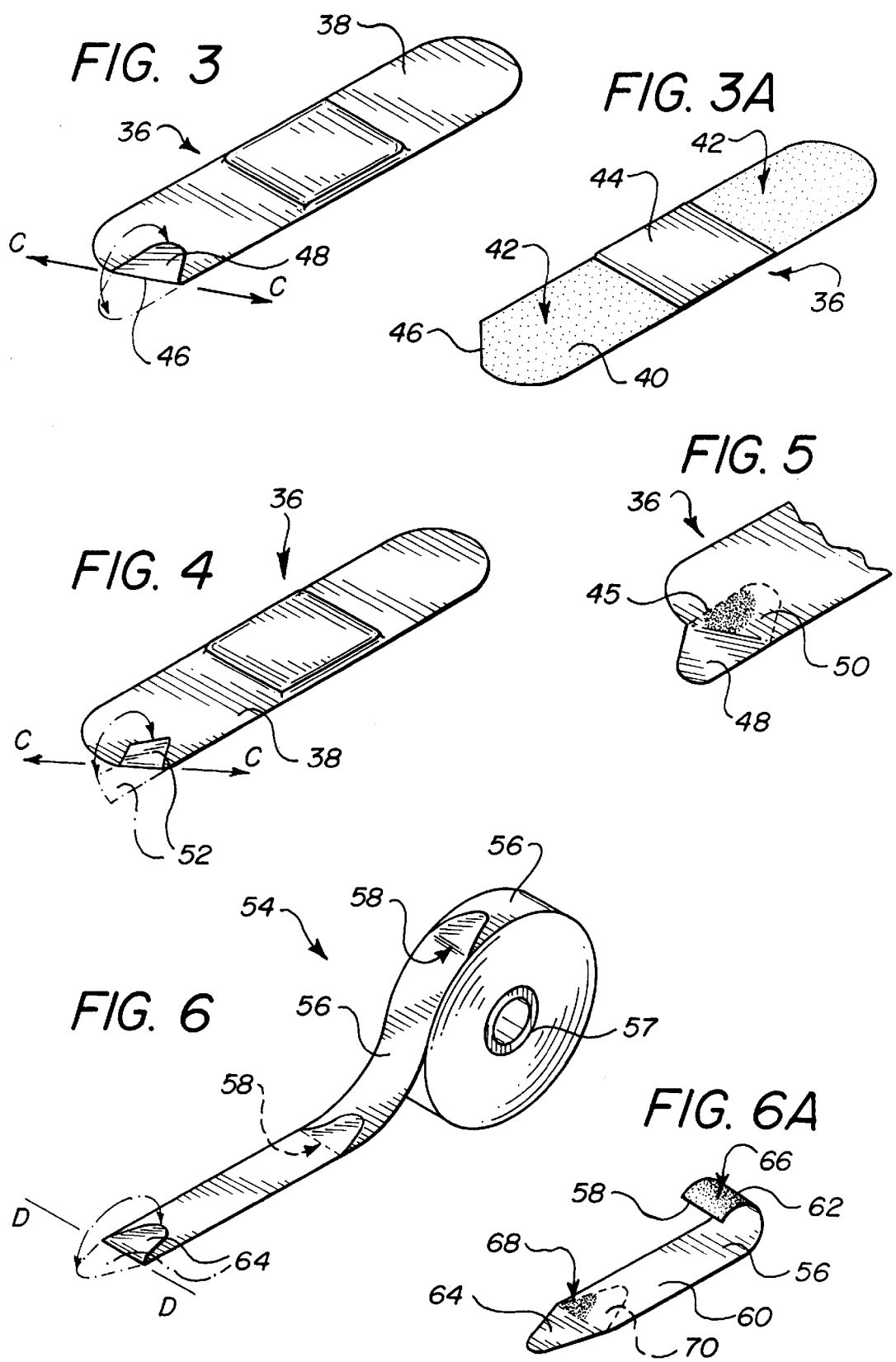

5,772,623

BANDAGE HAVING A TAB PORTION FOR FACILITATING EASY REMOVAL FROM THE SKIN

BACKGROUND OF THE INVENTION

The present invention generally relates to bandages and surgical dressings, and more specifically to bandages which are easily removeable from the skin.

Some form of bandages have always been used to protect open wounds by covering them, thereby preventing infection or reopening of the wound. Conventionally, bandages have been comprised of an elongated piece of flexible material having a cotton pad adhered to a middle portion of one side, a pressure sensitive adhesive coating the remainder of that side, cover paper covering the adhesive until use, and with the opposite side being untreated. When the bandage is to be placed over a wound, the cover paper is removed from the adhesive, and the bandage is securely placed on the skin with the cotton pad over the wound.

With small lacerations such as paper cuts or other non-serious wounds, the bandage used would have a fairly sticky adhesive applied thereto, thereby making removal of the bandage difficult, but not unattainable for the average person. However, people with limited dexterity may have considerable trouble peeling the bandage away from the skin. Despite this limitation with conventional bandages, more problematic are surgical dressings used to cover and facilitate healing of an incision made during surgery, or for covering some other serious wound. The traditional surgical dressing's adhesive adheres far more securely than the conventional bandages, and frequently require a doctor to use a scalpel or other sharp instrument to assist in peeling the dressing from the skin. This alone sometimes causes further cuts and wounds to the patient. When done repeatedly, as is the case with most surgical dressings, at a minimum this procedure hurts the patient and at worse cuts the patient seriously enough to warrant stitches.

It is therefore a principal object of the present invention to provide a bandage having a tab portion which may be easily grasped by a wearer of the bandage to ease the process of removing the bandage from the skin.

It is another object of the present invention to provide a bandage which is easily manufactured.

It is a further object of the present invention to provide a tab on a bandage which is intended to be grasped by the wearer but will not cause premature removal of the bandage.

Other objects will in part be obvious and in part appear hereinafter.

SUMMARY OF THE INVENTION

In accordance with the foregoing objects and advantages, the present invention provides a bandage of predetermined configuration having lower and upper surfaces. The lower, skin contacting surface is coated with a pressure sensitive adhesive substance of a first adhesive strength, and a cotton pad covering a predetermined area in the approximate center of the surface. The upper surface is primarily untreated with the exception of pressure sensitive adhesive of a second adhesive strength coating small areas adjacent the corners or edges of the bandage. The second adhesive strength is only 5% to 70% as strong as the first adhesive strength.

A tab portion fixedly attached to and extending from the corners or edges of the bandage is folded back upon the upper surface in complete covering relation to the adhesive. Therefore, after the bandage has been securely placed over a wound for the desired time period, and the bandage is to be removed from the skin, the person removing the bandage may simply pry the tab upwardly away from the bandage's upper surface, grasp the tab, and pull the bandage away from the skin. Thus, the tab eliminates the need for the person removing the bandage from having to pry between the skin and the bandage's lower surface, thereby risking further injury or irritation to the patient.

The purpose of securing the tab to the upper surface with a pressure sensitive adhesive weaker than the adhesive used to secure the bandage to the skin is to make it easy for the person removing the bandage to manipulate the tab while still ensuring that the tab remains fixed to the upper surface until it is desired to remove the bandage. If the tab was not secured to the upper surface, it is possible, if not probable, that the tab would become caught or snagged in some manner, thereby prematurely pulling the bandage from the skin.

BRIEF DESCRIPTION OF THE DRAWINGS

The invention will be further described in connection with the accompanying drawings, in which:

FIG. 1 is a perspective view of a surgical dressing having tabbed corners;

FIG. 1A is a fragmentary view of a tabbed corner of FIG. 1;

FIG. 1B is a bottom plan view of FIG. 1;

FIG. 2 is a perspective view of an alternate embodiment of the invention to FIG. 1;

FIG. 2A is a fragmentary view of a tabbed potion of FIG. 2;

FIG. 3 is a perspective view of a bandage having a tabbed corner;

FIG. 3A is a bottom plan view of FIG. 3;

FIG. 4 is a perspective view of an alternate embodiment of the invention of FIG. 3;

FIG. 5 is a fragmentary view of a tabbed portion of FIG. 4;

FIG. 6 is a perspective view of a roll of surgical tape having tabs positioned at spaced intervals;

FIG. 6A is a perspective view of one strip of surgical tape;

DETAILED DESCRIPTION

Figure 7:
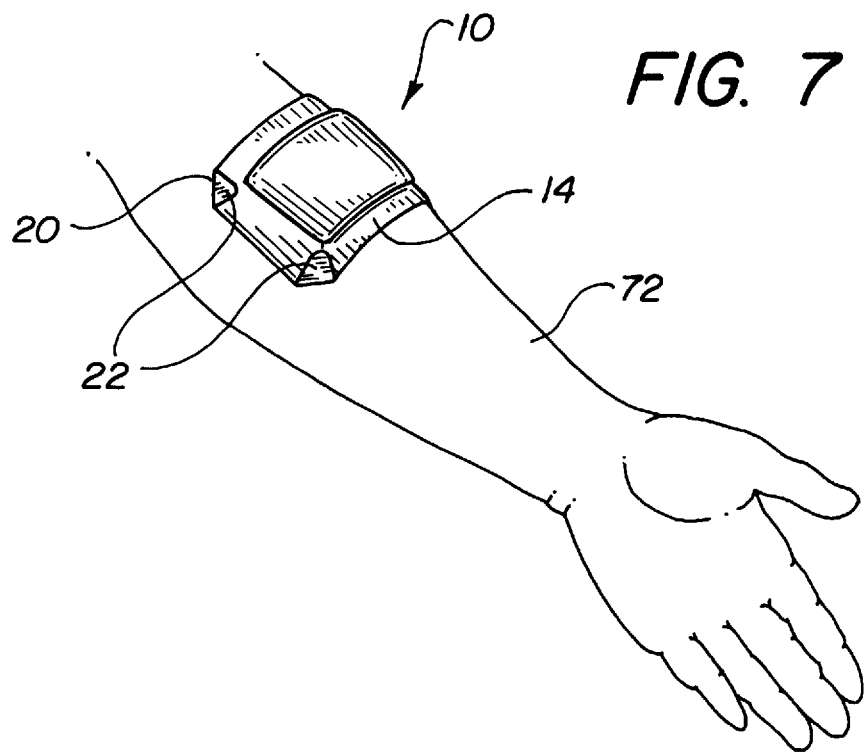
FIG. 7 is a perspective view of the dressing of FIG. 1 positioned on an arm.

Referring now to the drawing figures wherein like reference numerals refer to like parts throughout, there is seen in the FIGS. 1 a surgical dressing denoted generally by reference numeral 10. Dressing 10 is the type of bandage typically used to cover a surgical incision or other serious wound.

Dressing 10 is generally rectangular in shape, and includes lower and upper surfaces 12 and 14, respectively. Lower, skin contacting surface 12 is completely coated with a pressure sensitive adhesive 15, and a cotton, wound covering pad 16. Upper surface 14 is essentially untreated except for a pressure sensitive adhesive 18 coating a small portion of the upper surface 14 adjacent the obliquely cut corner edges 20 (FIG. 1A showing adhesive 18 in one corner is representative of all the corners of dressing 10). Dressing 10 further includes substantially triangularly shaped tab portions 22 integrally extending from corners 20, and which are secured in complete covering relation to adhesive 18 and in covering relation to a small untreated area 24.

Dressing 10 is manufactured with corners 20 being cut along a straight, oblique edge. Therefore, once tabs 22 are lifted from adhesive 18 they will be pivotal about oblique axis A—A.

Untreated areas 24 permit a finger tip or finger nail to easily grasp and pry upwardly on tabs 22, thereby effectivly freeing tabs 22 from adhesive 18. The strength of adhesive 18 is between 5%–70% as strong as adhesive 15. Therefore, tabs 22 will become detached from upper surface 14 quite easily. However, the strength of adhesive 18 is great enough to prevent tabs 22 from becoming detached therefrom absent some external prying force applied upwardly to tabs 22. Therefore, tabs 22 will not cause dressing 10 to be removed prematurely.

The strength of adhesive 15 varies for different kinds of bandages. Therefore, depending on the strength of adhesive 15, an adhesive strength of adhesive 18 between 5% to 70% of the strength of adhesive 15 should be sufficient for all bandages.

The FIGS. 2 represent an alternate embodiment of the dressing 10 shown in FIG. 1. Dressing 10' includes an upper surface 25, and a lower surface (not shown) which are identical to dressing's 10 lower and upper surfaces 12 and 14, respectively.

Dressing 10', like dressing 10, is generally rectangular in configuration. However, instead of having tabs at the corners of the dressing, dressing 10' includes elongated tabs 26 extending along the entire length of the two shorter side edges 28 and 30 of dressing 10'. Tabs 26 are foldable about longitudinal axis B—B, and are adhered to adhesive areas 32 which coat upper surface 25 at spaced intervals adjacent edges 28 and 30 (FIG. 2A only shows the areas adjacent edge 28, but the areas adjacent edge 30 are substantially identical). Like dressing 10, dressing 10' also includes untreated areas 34 which lie in covered relation to tabs 26. Areas 34 permit a finger tip or finger nail to engage tabs 26 and pry upwardly thereon in order to detach tabs 26 from adhesive 32.

As is the case with the adhesives of dressing 10, adhesive 32 of dressing 10' is only 5% to 70% as strong as the adhesive used on the bottom surface.

Referring now to FIGS. 3–5 there is seen a bandage, denoted generally by reference numeral 36, typically used for small cuts and abrasions. Bandages similar to bandage 36 are the BAND-AID® brand bandages, manufactured by Johnson and Johnson Corporation.

Bandage 36 is generally longitudinally elongated in shape and includes upper and lower surfaces 38 and 40, respectively. Lower, skin contacting surface 40 is completely covered with an adhesive 42 and includes a gauze pad 44 fixedly, centrally positioned thereon. Upper surface 38 is generally untreated with the exception of a small amount of adhesive 45 coating a portion of upper surface 38 adjacent a straight, oblique edge 46. An essentially triangularly shaped tab 48 integrally extends from oblique edge 46 and lies in complete covering relation to adhesive 44 as well as in covering relation to a non-treated area 50. Thus, tab 48 is adhered to upper surface 38 until an external force detaches tab 48 from upper surface 38.

Tab 48 may be pried upwardly away from upper surface 38 by a finger tip or finger nail engaging the portion of tab 48 which lies in covering relation to non-treated area 50; gripping tab 48 between two fingers; and then pulling upwardly on tab 48. Adhesive 44 is only about 5% to 70% a strong as adhesive 42, and therefore provides a fairly weak adhesive force to overcome. Once detached from upper surface 38, tab 48 is pivotal about oblique axis C—C which extends along oblique edge 46.

FIG. 4 shows bandage 36 with an essentially trapezoidal shaped tab 52, as opposed to triangularly shaped tab 48. Tab 52 adheres to upper surface 38 in the identical manner as does tab 48. Tab 52 is also pivotal about oblique axis C—C.

Referring now to FIG. 6 there is seen a roll of surgical tape denoted generally by reference numeral 54. Tape roll 54 includes a plurality of surgical tape strips 56 which are wound upon a central spool 57, and are independently separable from roll 54 by tearing a strip along its perforated edge 58. Tape strips 56 are used to fasten a gauze pad, IV, or the like to a patient's skin.

Each strip 56 includes upper and lower surfaces 60 and 62, respectively, and a tab 64 integrally extending from perforate edge 58. Lower surface 62 is completely covered with pressure sensitive adhesive 66. Upper surface 60 is essentially untreated except for a small amount of adhesive 68 coating upper surface 60 adjacent tabbed end 65. Tab 64 lies in complete covering relation to adhesive 68 and in covering relation to untreated area 70.

When it is necessary to remove a strip 56 from a patient, a finger tip or finger nail can engage the portion of tab 60 above untreated area 70 and pry tab 60 upwardly away from upper surface 60. When free, tab 60 is pivotal about axis D—D. Tab 60 can then be grasped and used to pull tape strip 56 away from the patient's skin.

Figure 8:
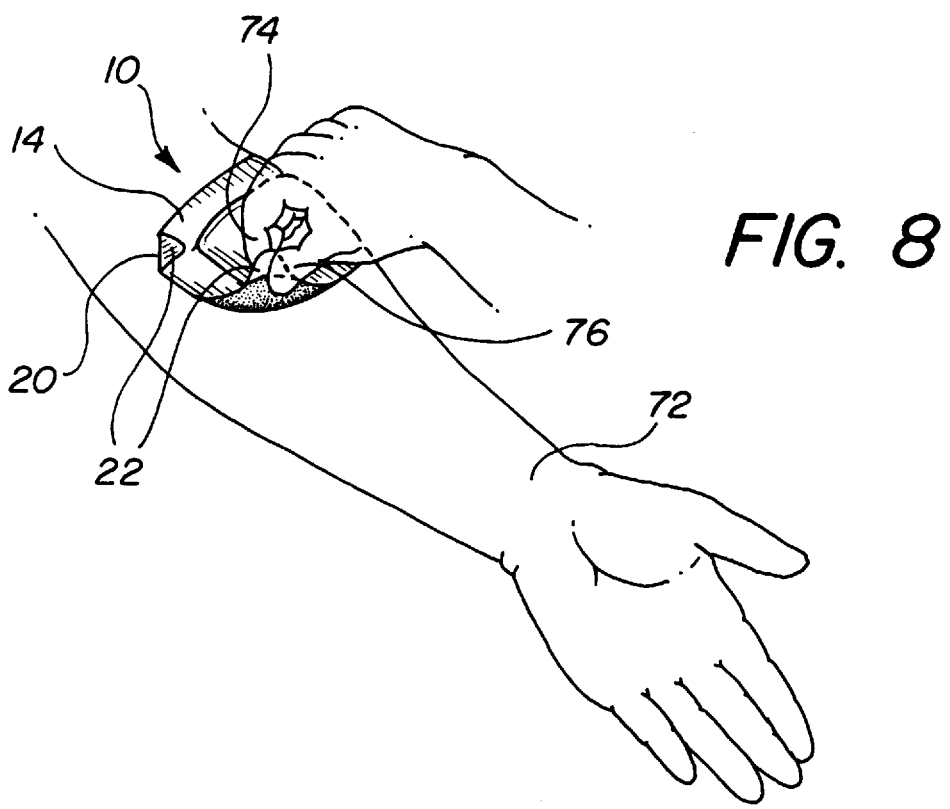
FIG. 8 is the perspective view of FIG. 7 showing the dressing being removed.

FIGS. 7 and 8 illustrate the method of removing the bandage of the present invention from a patient's skin. As illustrated, the bandage shown is dressing 10 of FIG. 1 and the bandage is applied to the skin of a patient's arm 72. It should be understood that any type of bandage encompassed by the claims of this application would operate in the manner described hereinafter. Furthermore, arm 72 is for illustrative purposes only, as the bandage could be applied to any portion of the skin.

FIG. 7 shows dressing 10 attached to a person's arm 72, while FIG. 8 shows dressing 10 being removed from arm 72. As was previously discussed, to remove dressing 10 from arm 72, first, a finger tip 74 engages the portion of tab 22 above untreated area 24. Second, tab 22 is grasped between finger tip 74 and another finger 76. Third, tab 22 is pulled upwardly until it is detached from upper surface 14. Fourth and finally, tab 22 remains grasped between fingers 74 and 76 and dressing 10 is peeled in a direction to remove it from arm 72. Accordingly, there is no need to pry into arm 72 in order to peel off dressing 10. In the event that the tab 22 used to peel off dressing 10 rips off, one of the other tabs 22 can be manipulated in this identical manner.

What is claimed is:

1. An adhesive flat bandage having at least one edge defining a predetermined periphery, each of said at least one edge having a respective axis extending therealong, said bandage used to cover a wound to the skin, said bandage comprising:

a) a lower surface having a coating of first adhesive thereon, said first adhesive being of a first adhesive strength;

b) an upper surface having a partial coating of a second adhesive thereon, said second adhesive being of a second adhesive strength; and c) at least one tab integrally extending outwardly from said at least one edge, said tab being foldable backwardly upon itself about said respective axis extending along said at least one edge and positioned in releasably adhered relation to said upper surface in covering relation to said second adhesive, whereby said tab may be detached from said upper surface and manipulated to pull said bandage away from said skin.

2. The invention according to claim 1 wherein said first adhesive is stronger than said second adhesive.

3. The invention according to claim 2 wherein said second adhesive is from 5% to 70% as strong as said first adhesive.

4. The invention according to claim 1 wherein said bandage is substantially rectangular in shape, thereby said bandage includes four edges and four corners.

5. The invention according to claim 4 wherein each of said four corners are obliquely cut along a straight edge, thereby said bandage includes four sides and four obliquely cut corners having a respective oblique axis extending along said corners.

6. The invention according to claim 5 wherein said second adhesive is coated on a portion of said upper surface adjacent at least one of said four corners.

7. The invention according to claim 6 wherein said at least one tab integrally extends from at least one of said four obliquely cut corners, said at least one tab being foldable about a said respective oblique axis, and is removably adhered to said upper surface in covering relation to said second adhesive.

8. The invention according to claim 7 wherein said at least one tab is removably adhered to said upper surface in covering relation to said second adhesive and to a predetermined non-adhesive area of said upper surface, whereby said tab is adhered to said upper surface in a manner conducive for unobstructed grasping thereof.

9. The invention of claim 7 wherein said at least one tab is substantially triangular in shape.

10. The invention according to claim 4 wherein said bandage includes first and second edges of a first length, and third and fourth edges of a second length, said first length being longer than said second length.

11. The invention according to claim 9 wherein said at least one tab integrally extends from at least one of said first and second edges, said tab being releasably adhered to said upper surface in covering relation to said second adhesive.

12. The invention according to claim 11 wherein said at least one tab is removably adhered to said upper surface in covering relation to said second adhesive and to a predetermined, non-adhesive area of said upper surface, whereby said at least one tab is adhered in a manner conducive for unobstructed grasping thereof.

13. The invention according to claim 11 wherein said at least one tab is elongated in shape.

14. The invention according to claim 8 wherein said second adhesive is coated on a portion of said upper surface adjacent at least one of said first and second short edges.

15. The invention according to claim 1 wherein said bandage is longitudinally elongated in shape and said periphery is defined by first and second, opposed, long edges and first and second, opposed, curvi-linear, short edges.

16. The invention according to claim 15 wherein at least one of said first and second opposed, curvi-linear edges includes a linear, oblique edge forming a portion thereof.

17. The invention according to claim 16 wherein said second adhesive is coated on a portion of said upper surface adjacent said at least one, linear, oblique axis.

18. The invention according to claim 17 wherein said at least one tab integrally extends from said at least one linear, oblique edge, said at least one tab being removably adhered to said upper surface in covering relation to said second adhesive.

19. The invention according to claim 18 wherein said at least one tab is removably adhered to said upper surface in covering relation to said second adhesive and to a predetermined, non-adhesive area of said upper surface in a manner conducive for unobstructed grasping thereof.

* * * * *